US00PP33768P2

(12) United States Plant Patent
Van Swieten

(10) Patent No.: US PP33,768 P2
(45) Date of Patent: Dec. 21, 2021

(54) ***PHALAENOPSIS* ORCHID PLANT NAMED 'PHALISCON'**

(50) Latin Name: ***Phalaenopsis* hybrid**
Varietal Denomination: PHALISCON

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,546

(22) Filed: Aug. 11, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALISCON', particularly characterized by having white, small, shaded flowers with greenish-yellow and very light purple lips, flowers that are flat in lateral view, 5 to 7 branches, and is propagated by meristem tissue culture, is disclosed.

3 Drawing Sheets

Genus and species: *Phalaenopsis* hybrid.
Variety denomination: 'PHALISCON'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALISCON'.

The new *Phalaenopsis* plant is a product of a planned breeding program conducted by the inventor in Bleiswijk, the Netherlands. The objective of this breeding program was to create a new, branched *Phalaenopsis* plant with white, small, shaded flowers with greenish-yellow and very light purple lips, suitable for potted plant production.

The new *Phalaenopsis* plant 'PHALISCON' is a result of cross-pollination made by the inventor in January 2011 in Bleiswijk, the Netherlands, of the proprietary female, or seed parent, *Phalaenopsis* hybrid '27490-07' (unpatented) with the proprietary male, or pollen parent, *Phalaenopsis* hybrid '01-3358' (unpatented).

The new *Phalaenopsis* was selected by the inventor as a single plant within the progeny of the stated cross-pollination in a controlled greenhouse in Bleiswijk, the Netherlands, in January 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 20, 2019 (Application no. 2019/2310), by Applicant who obtained the subject matter disclosed directly from the inventor. 'PHALISCON' has not been made publicly available or sold anywhere in the world prior to the effective filing date of this application with the exception of sales or disclosures made one year or less before the effective filing date of this claimed invention by Applicant who obtained 'PHALISCON' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALISCON' as a new and distinct variety of *Phalaenopsis* plant:

1) White, small, shaded flowers with greenish-yellow and very light purple lips;
2) Flower shape in lateral view is flat; and
3) Plant has 5 to 7 branches.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2021. Colors in the photographs may differ from the color values cited in the detailed botanical description, which accurately describe the actual colors of the new variety.

DESCRIPTION OF THE NEW VARIETY

Figure 1:
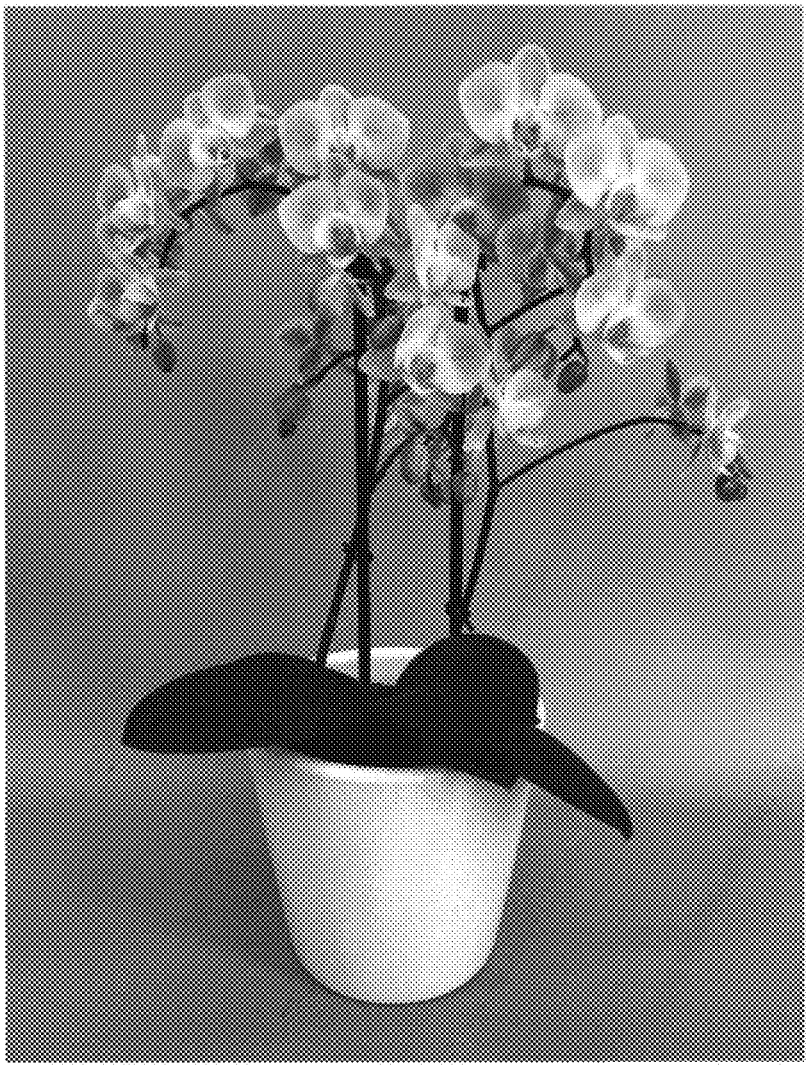
FIG. 1 shows the overall plant habit, including blooms, buds, and foliage of 'PHALISCON'.
Figure 2:
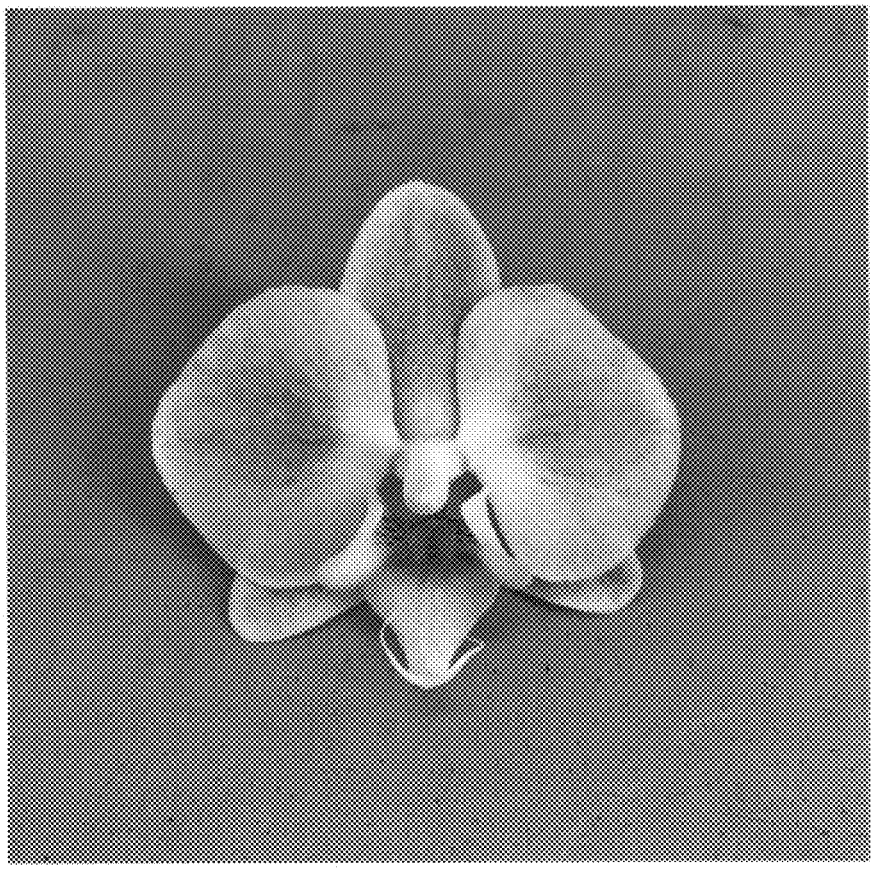
FIG. 2 shows a close-up of a flower of 'PHALISCON'.
Figure 3:
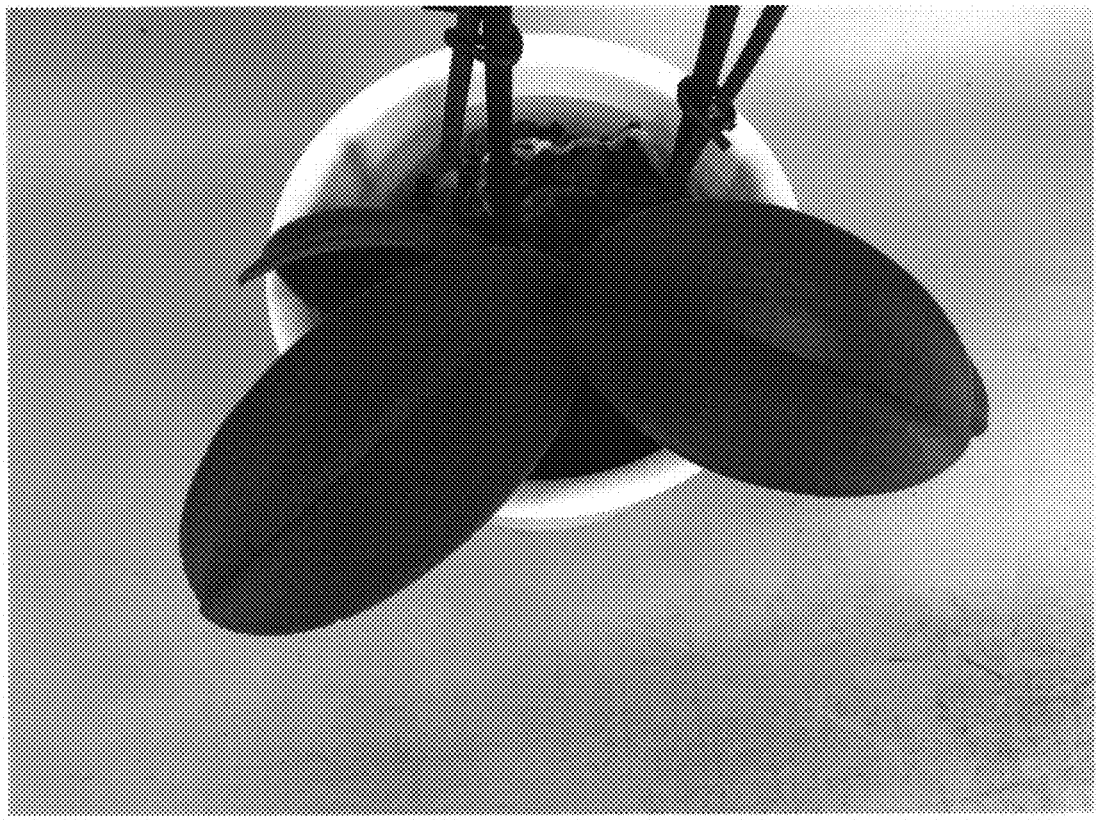
FIG. 3 shows an overhead view of the leaves of 'PHALISCON'.

The following detailed description sets forth the distinctive characteristics of 'PHALISCON'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALISCON'.

Parentage:
- *Female parent*.—*Phalaenopsis* cultivar '27490-07' (unpatented).
- *Male parent*.—*Phalaenopsis* cultivar '01-3358' (unpatented).

Propagation:
- *Type*.—Meristem tissue culture.

Roots:
- *Root description*.—Greyed-green (a color in between RHS 190B and RHS 190C) colored roots with branching lateral roots having yellow-green (a color in between RHS N144A and RHS 151A) colored root tips.

Plant:
- *Crop time to flowering*.—Following asexual propagation (in vitro), the rooted cuttings grow for 20-24 weeks. After transplantation into 12-cm pots, the plants are finished after 48 to 50 weeks.
- *Growth habit of the peduncle*.—Upright to slightly pendent with panicle inflorescence.
- *Height* (*from soil level to top of inflorescence*).—Approximately 33.0 cm to 38.0 cm.
- *Width* (*measured from leaf tips*).—About 21.0 cm to 24.0 cm.
- *Vigor*.—Strong.

Leaves:
- *Mature leaves*.—Quantity per plant: 7 to 9 leaves are produced before flowering. Length (fully expanded): 11.0 cm to 13.0 cm. Width: 5.0 cm to 6.0 cm. Position of the broadest part of the leaf: At the middle. Shape: Oblong. Base shape: Moderately to slightly elongated. Apex: Unequal obtuse. Leaf blade angle with the petiole (measured from the horizontal position): Between 10 degrees and 25 degrees. Leaf margin: Entire. Color: Upper surface: RHS 147A. Lower surface: RHS 146B with a touch of purple (RHS N77A). Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146B.

Peduncle:
- *Quantity per plant*.—1 to 2.
- *Number of flowers per peduncle*.—18 to 24.
- *Length*.—33.0 cm to 38.0 cm.
- *Diameter*.—3.0 mm to 4.0 mm.
- *Strength*.—Strong.
- *Aspect*.—Upright to slightly pendent.
- *Texture*.—Smooth.
- *Color*.—Green (RHS 146A) with a touch of purple (RHS N77A).
- *Internode length*.—2.0 cm to 3.0 cm.

Inflorescence description:
- *Appearance*.—Upright to slightly pendent, panicle inflorescence with bilaterally symmetrical flowers that open in succession beginning with the lowermost flower.
- *Number of inflorescences*.—1 to 2.
- *Inflorescence size*.—Height (from base to tip): 330.0 mm to 360.0 mm.
- *Flowering time*.—First flowers can be expected 10 to 11 months after planting in a 12-cm pot.
- *Flower*.—Height: 40.0 mm to 45.0 mm. Diameter: 50.0 mm to 55.0 mm. Depth of lip: 18.0 mm to 20.0 mm.
- *Flower longevity*.—On the plant: 10 to 12 weeks.
- *Flower shape*.—Flat.
- *Fragrance*.—Absent.
- *Flower bud*.—Average size: Medium. Length: 15.0 mm to 17.0 mm. Width: 11.0 mm to 13.0 mm. Shape: Egg shaped. Color: Light yellow-green (RHS 145B and RHS 145C) with a purplish-red shade (RHS N77B) and reddish-purple stripes (RHS N78B).
- *Petals*.—Arrangement: Open/free. Shape: Semi-circular. Apex: Obtuse asymmetric. Margin: Moderately undulated. Length (from base to tip): 29.0 mm to 31.0 mm. Width: 23.0 mm to 25.0 mm. Position of the broadest part of the petal: Toward the base. Color (when fully opened): Upper surface: Basic color: White (RHS NN155C). Over color: Light purple shade (RHS N75B) and few light reddish-purple stripes (RHS N78D). Lower surface: Basic color: White (RHS NN155C). Over color: Light reddish-purple shade (RHS N78D). Number of spots and stripes on the petals (upper surface): Few stripes. Color of spots and stripes on the petals (upper surface): RHS N78D. Density of netting of the petals (upper surface): None. Color of the netting (upper surface): Not applicable.
- *Dorsal sepal*.—Shape: Elliptic. Apex: Obtuse symmetric. Margin: Entire. Length (from base to tip): 25.0 mm to 27.0 mm. Width: 15.0 mm to 17.0 mm. Position of the broadest part of the dorsal sepals: At the middle. Color (when fully opened): Upper surface: Basic color: White (RHS NN155C). Over color: Light purple (RHS 76A). Lower surface: Basic color: White (RHS NN155C). Over color: Light reddish-purple (RHS N78D); reddish-purple midvein (RHS N78B). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse symmetric. Margin: Entire. Length (from base to tip): 24.0 mm to 26.0 mm. Width: 15.0 mm to 17.0 mm. Position of the broadest part of the lateral sepals: At the base. Color (when fully opened): Upper surface: Basic color: White (RHS NN155C). Over color: Light yellow-green (RHS 145D) at the base and light purple (RHS 76A). Lower surface: Basic color: White (RHS NN155C). Over color: Light yellow-green (RHS 157C) at the base; light reddish-purple (RHS N78D) and reddish-purple midvein (RHS N78A). Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 10.0 mm to 12.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 14.0 mm to 16.0 mm. Width: 10.0 mm to 12.0 mm. Color: Upper surface: Touch of light yellow-green (RHS 4D) and striped (RHS 183B) at the base; greenish-yellow margin (RHS 151B) on one side; white (RHS NN155C) toward other side and tip. Lower surface: White (RHS NN155C); greenish-yellow margin (RHS 151B) on one side. Number of spots and stripes on the lateral lobe: Medium stripes. Color of spots and stripes on the lateral lobe: RHS 183B. Density of netting of the lateral lobe: None. Color of the netting: Not applicable.

*Apical lobe*.—Shape: Triangular. Margin: Entire. Length: 16.0 mm to 18.0 mm. Width: 13.0 mm to 15.0 mm. Color: Upper surface: Greenish-yellow (RHS 151D) at the base and toward wings; white (RHS NN155C) with diluting very light purple shade (RHS 76B) toward whiskers. Lower surface: Light reddish-purple (RHS N78D) at the middle from base toward whiskers; greenish-yellow wings (RHS 151B); white margins (RHS NN155C) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 4.0 mm to 5.0 mm. Length: 4.0 mm to 5.0 mm. Width: 2.0 mm to 3.0 mm. Color: Greenish-yellow (RHS 5B) and light yellow-green (RHS 157C) on sides; dotted (RHS 183B).

Reproductive organs:

*Column*.—Length: 9.0 mm to 10.0 mm. Diameter: 3.0 mm to 4.0 mm. Color: White (RHS NN155C) with purplish-pink dot (RHS N78C) toward the tip.

*Pollinia*.—Quantity: 2. Diameter: 0.7 mm to 0.9 mm. Color: Orange-yellow (RHS 23A).

*Ovary*.—Length: 8.0 mm to 10.0 mm. Diameter: 1.6 mm to 1.8 mm.

*Pedicel*.—Length: 25.0 mm to 27.0 mm. Diameter: 1.9 mm to 2.1 mm. Color: Light yellow-green (RHS 145C) and light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALISCON' differs from the female parent plant '27490-07' (unpatented) in that 'PHALISCON' has flowers with a shaded pattern and apical lobes with a main color of greenish-yellow, whereas '27490-07' has flowers with a small center pattern and apical lobes with a main color of light purple.

'PHALISCON' differs from the male parent plant '01-3358' (unpatented) in that 'PHALISCON' has obtuse dorsal sepal apexes and apical lobes with a main color of greenish-yellow, whereas '01-3358' has emarginated dorsal sepal apexes and apical lobes with a main color of reddish-purple.

'PHALISCON' is most similar to the commercial *Phalaenopsis* plants named 'PHALIJBAK' (U.S. Plant Pat. No. 32,935) and 'PHALWALWHO' (U.S. Plant Pat. No. 33,393). 'PHALISCON' differs from the commercial variety 'PHALIJBAK' in that 'PHALISCON' has white whiskers and flowers with a shaded pattern, whereas 'PHALIJBAK' has purplish-pink whiskers and flowers with a striped pattern.

'PHALISCON' differs from the commercial variety 'PHALWALWHO' in that 'PHALISCON' has obtuse dorsal sepal apexes and columns that are white with a purplish-pink dot toward the tip, whereas 'PHALWALWHO' has slightly emarginated dorsal sepal apexes and columns that are very light purple with light reddish-purple tip.

I claim:

1. A new and distinct variety of *Phalaenopsis* plant named 'PHALISCON', substantially as described and illustrated herein.

* * * * *